United States Patent [19]

Ferguson et al.

[11] Patent Number: 5,019,505
[45] Date of Patent: May 28, 1991

[54] ENZYMES HAVING ALPHA-GLYCEROL-3-PHOSPHATE OXIDASE ACTIVITY, PRODUCTION AND USE THEREOF

[75] Inventors: Clare H. R. Ferguson, St. Stephens; Anne M. Macadam, Canterbury; Jane E. Ince, Canterbury; Christopher J. Knowles, Canterbury, all of England

[73] Assignee: GEnzyme (U.K.) Ltd., England

[21] Appl. No.: 75,941

[22] Filed: Jul. 22, 1987

[30] Foreign Application Priority Data

Jul. 29, 1986 [GB] United Kingdom ............... 8618469

[51] Int. Cl.$^5$ .................. C12P 7/26; C12N 9/04; C12Q 1/26
[52] U.S. Cl. .................. 435/148; 435/190; 435/25
[58] Field of Search .................. 435/190, 25, 148

[56] References Cited

U.S. PATENT DOCUMENTS

| | | | |
|---|---|---|---|
| 4,166,005 | 8/1979 | Masurekar et al. | 435/190 |
| 4,241,178 | 12/1980 | Esders et al. | 435/15 |
| 4,275,161 | 6/1981 | Misaki et al. | 435/190 |
| 4,463,095 | 7/1984 | Emi et al. | 435/190 |

OTHER PUBLICATIONS

Sone, N. (1972) J. Biochem. 71, 931–940.
Sone, N. et al. (1972) J. Biochem 72, 291–297.
Sone, N. (1973) J. Biochem. 74, 297–305.
Fairlamb, A. H. et al. (1978) Chem. Abst. 88:146007w.
Hill, G. C. et al. (1980) Chem. Abst. 93:64601z.
Chemical Abstracts, vol. 101, Nov. 1984, p. 538, Abstract No. 169098c.

*Primary Examiner*—Elizabeth C. Weimar
*Assistant Examiner*—Charles L. Patterson, Jr.
*Attorney, Agent, or Firm*—Bacon & Thomas

[57] ABSTRACT

An enzyme having α-glycerol-3-phosphate oxidase activity characterized in that it has a Km of less than 2.5 mM is disclosed, as is the production and use thereof.

More particularly, such enzymes may be obtained from Propionibacterium species and may have Km values of less than 50 μM, hence are advantageous for triglyceride/glycerol/α-glycerol-3-phosphate determinations and test kits.

8 Claims, No Drawings

ENZYMES HAVING ALPHA-GLYCEROL-3-PHOSPHATE OXIDASE ACTIVITY, PRODUCTION AND USE THEREOF

This invention relates to enzymes having α-glycerol-3-phosphate oxidase activity and to the production and use thereof; more particularly, it relates to such enzymes which are advantageous for triglyceride/glycerol/α-glycerol-3-phosphate determinations and test kits.

For present purposes, α-glycerol-3-phosphate-oxidase, α-GPO, (EC 1.1.3.21), is conventionally extracted from lactic acid bacteria, such as 'Aerococcus viridans' (NCIMB 11776), see for example, U.S. Pat. No. 4,275,161 and German 2,737,288. Also, reference has previously been made to an NAD-independent α-glycerol-3-phosphate dehydrogenase obtained from 'Propionibacterium acidi-propionici' (formerly 'arabinosum'), which is located in minute particles, see, for example, Sone, J. Biochem: 71, 931–940; 72. 291–297; 74. 297–305).

The present invention provides an enzyme having α-glycerol-3-phosphate oxidase activity characterised in that it has a Km of less than 2.5mM, preferably less than 50μM. Such may be obtained from a 'Propoionibacterium' species; more particularly, it may be obtained from 'P. freudenreichii' subsp. 'freudenreichii' or 'shermanii' or 'P. acidi-propionici. Specifically, the present invention relates to such an enzyme which is obtained from 'P. freuednreichii' subsp. 'freudenreichii' (DSM 20270 or NCIMB 5959) or 'shermanii' (NCIMB 9885, 5964 or 9416) or 'P. acidi-propionici'(NCIMB 5958) and has a Km of about 15μM, 26μM, 22μM, 6μM, 18μM or 18μM, respectively.

The present invention also provides a process for the production of such an enzyme characterized in that it comprises culturing an appropriate bacterium, harvesting and disrupting the cells, separating a cell-free extract and at least partially purifying the desired enzyme. Such production is generally conventional.

The present invention further provides the use of such an enzyme to catalyze the oxidation of α-glycerol-3-phosphate. In one embodiment, the present invention provides a method of triglyceride/glycerol/αglycerol-3-phosphate determination characterised in that it comprises providing a sample containing α-glycerol-3-phosphate, reacting the αglycerol-3-phosphate with such an enzyme to produce hydrogen peroxide and determining the hydrogen peroxide to give the desired indication, the α-glycerol-3-phosphate optionally having been produced from glycerol previously and the glycerol optionally having been produced from triglyceride previously. In another emdodiment, the present invention provides a test kit for triglyceride/glycerol/α-glycerol-3-phosphate determination characterised in that it comprises means for providing a sample containing α-glycerol-3phosphate, such an enzyme for reaction therewith and means for determination of hydrogen peroxide produced, also optionally means for providing an α-glycerol-3-phosphate containing sample from a glycerol-containing sample and optionally means for providing a glycerol containing sample from a triglyceride-containing sample.

Inasmuch as the substrate of an enzyme in accordance with the present invention is α-glycerol-3-phosphate and bearing in mind that triglyceride may be converted to glycerol and that glycerol may be converted to α-glycerol-3-phosphate, the present invention may be useful in the determination of any or all thereof. By way of illustration, the present invention may be applied to the determination of triglycerides and/or glycerol from various sources, for example the estimation of triglycerides in foodstuffs and in the blood. Samples may include solids and, in particular, liquids and biological fluids, such as serum.

'Inter alia', the present invention relates to a particularly advantageous α-glycerol-3-phosphate oxidase which may be obtained from 'Propionibacterium freudenreichii'subsp. 'freudenreichii' (DSM 20270), for example. The production thereof is generally conventional. As indicated above, such low Km enzymes may also be obtained from other species of the genus 'Propionibacterium', for example, 'P. 'acidi-propionici' (formerly arabinosum) (NCIMB 5958) and 'P. 'freudenreichii' subsp. 'shermanii' (formerly 'shermanii') (e.g. NCIMB 9885). The restricted distribution of such enzymes is notable. Contrary to expectation, such have not been found in species of genera such as Cellulomonas. e.g. 'C. 'flavizena' (NCIMB 8073), 'C. celida' (NCIMB 8076) and 'C. 'subalbus' (NCIMB 8075), 'Micrococcus' e.g. 'M. luteus' (NCIMB 8553) and 'M. varians' (NCIMB 8609), 'Brevibacterium', e.g. R312 (UKC Culture Collection), 'Corvnebacterium'. e.g. 'C. 'glutamicum' (NCIMB 21516), and 'Arthrobacter', e.g. 'A. 'globiformis' (NCIMB 8602). See, for example, Kandler, Developments in Industrial Microbiology, '25', 109–123, and Jones, J. Gen. Microbiol, '87', 52–96.

The preferred enzyme provided by the present invention is a soluble oxidase which catalyses the following reaction:

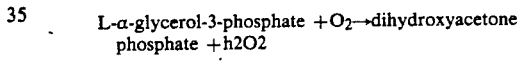

L-α-glycerol-3-phosphate $+O_2 \rightarrow$ dihydroxyacetone phosphate $+h2O2$

The enzyme only uses L-G3P and does not react with D-G3P. The reaction takes place stoichiometrically with the formation of hydrogen peroxide. This enzyme is a characteristic oxidase since it uses molecular oxygen as electron acceptor. (However, oxygen may be replaced by artificial acceptors, such as DCPIP, as the co-substrate. giving an increased rate of reaction (e.g. 18 fold).) Such enzyme is soluble (shown by high speed centrifugation) and, unlike the above-mentioned dehydrogenase, is not present in the minute particles. One of the properties of the present enzyme which would not be shared by an α-glycerol-3-phosphate dehydrogenase is that, on reacting with its substrates, 'viz' L-α-glycerol-3-phosphate and molecular oxygen, H2O2 is produced which may, 'inter alia' take part in a colour-producing reaction, such as the Trinder reaction, Ann. Clin. Biochem., '6', 24–27.

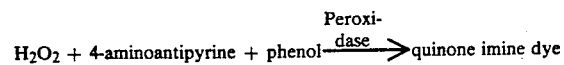

$H_2O_2$ + 4-aminoantipyrine + phenol $\xrightarrow{\text{Peroxidase}}$ quinone imine dye As indicated above, this opens the possibility of utilizing such an enzyme in a. method of determining, say, triglycerides, in particular in body fluids, such as serum, but also in foodstuffs, for example.

The presently-preferred enzyme obtainable from 'P. 'freudenreichii' subsp. 'freudenreichii' (DSM 20270) may be more particularly characterised as follows:

The molecular weight (determined by gel filtration on a Sephadex (Registered Trade Mark) G-200 column)

is 356,000. The sub-unit molecular weight (determined by SDS polyacrylamide gel electrophoresis) is 63,000. It is active between pH 6.0 and pH 8.0, with an optimum activity at about pH 7.5 in 0.1M dimethylglutarate buffer (DMG) and in 0.1M Na2HPO4/NaH2PO4 buffer, but the pH optimum is below pH 7.0 in 0.1M Tris-HCl. It catalyses the first-mentioned reaction and has a Michaelis-Menten constant (Km) in respect of its substrate, L-α-glycerol-3-phosphate, of $1.5 \times 10-2$mM (15μM). In this respect the present enzyme differs greatly from previously described examples of α-GPO all of which have Km values for L-α-glycerol-3-phosphate of 2.5mM or greater. The 170-fold lower Km value of the presently-preferred enzyme has great significance as the enzyme has much greater affinity for L-α-glycerol-3-phosphate allowing the sensitivity of the enzyme reaction to be greatly increased and reducing the amount of enzyme required for the measurement, for example, of serum triglycerides or in other assays involving determination of glycerol or L-α-glycerol-3-phosphate. In general terms, the enzymes according to the present invention have markedly reduced Km values. (It has been found that, as a co factor, the flavoprotein FAD stimulated activity 65% from the high.speed supernatant stage onwards in the purification.)

As indicated above, the production of, for example, the presently-preferred enzyme is generally conventional. For example, 'Propionibacterium freudenreichii' subsp. 'freudenreichii' (DSM 20270) may be grown in liquid culture. The cells may then be harvested and disrupted chemically or, preferably, mechanically. The disrupted cell homogenate may then be freed of particulate matter by centrifugation, for example. The α-GPO in the resulting cell-free extract may be further purified by conventional protein purification procedures, concentrated and freeze-dried.

Such an enzyme may, as mentioned above, be used in conjunction with the enzymes lipase, glycerol kinase and peroxidase and the chemicals phenol and 4-amino-antipyrine to measure the amounts of triglyceride in fluids according to the following reactions:

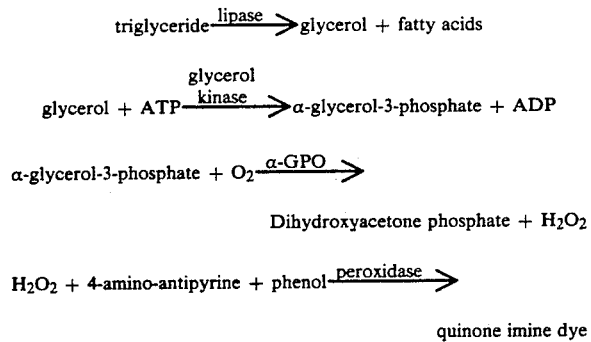

The present α-GPO is therefore useful for the specific determination of triglyceride, for example, which is an important diagnostic measurement for the identification of, 'inter alia', such diseases as chronic ischemic heart disease, arteriosclerosis, hyperlipoproteinaemia and extrahepatic biliary obstruction. An important advantage of the present enzyme over those previously described in such utility relates to its greatly superior affinity for its substrate, L-α-glycerol--phosphate.

The following exemplification illustrates the present invention:

'Growth of Propionibacterium freudenreichii subsp. freudenreichii (DSM 20270) and preparation of enzyme'

Freeze-dried cultures of 'Propionibacterium 'freudenreichii' subsp. 'freudenreichii' (DSM 20270) were obtained from Deutsche Sammlung von Mikroorganismen (DSM). Griesebachstrasse 8, D-3400 Gottingen, Federal Republic of Germany. A freeze dried ampoule was used to inoculate 100ml of medium containing glycerol (8g L−1), yeast extract (4g L−1), mycological peptone (2g L−1), K2HPO4 (5g L−1), NaH2PO4.2-H2O (lg L −1), CaCl2 (0.1mM), MgSO 4.7H2O (1.0mM) and trace quantities of cobalt, manganese, borate, copper and iron (II). The medium was sterilised by autoclaving and had an initial pH of 7.6. The cultures were allowed to grow without shaking at 30° C. for 48h. 25ml of this seed culture was used to inoculate 250ml of the same medium into a 500 ml bottle and the culture allowed to grow without shaking at 30° C. for 30–46h to reach stationary phase. (The level of GPO activity reached a maximum at the start of the stationary phase and then declined rapidly.) The microorganisms were harvested by centrifugation at 23,000 × g and resuspended in 0.01M Na2HPO4/NaH2PO4 buffer, pH 7.0 containing 0.5% (v/v) Triton (Registered Trade Mark) X-100 at 4° C. The cell suspension was subjected to disruption using a French pressure cell at a pressure of 7–8 tonnes. The suspension was passed through the pressure cell three times. Sonication may also be used for this purpose. The cell debris was removed from the homogenate by centriguation at 50,000 ×g. The supernatant was decanted and further centrifuged at 150,000 ×g for 90 minutes. (Growth in half rather than completely-filled bottles provided better aeration and resulted in increased growth and yield of activity.)

'Assay method'

Aliquots of the resulting supernatant containing partially purified α-GPO were used in the following test system:

| | |
|---|---|
| L-α-glycerol-3-phosphate | 0.05 mM |
| Phenol | 2.1 mM |
| Triton-X-100 | 0.05% |
| 4-amino-antipyrine | 1.5 mM |
| Peroxidase | 20 units |
| Dimethylglutarate buffer (DMG; pH 7.5) | 60 mM |

The rate of change of absorbance was measured at 505nm, 37° C. in a spectrophotometer. According to such test, the specific activity of the purified α-GPO was 30 munit/mg protein (a unit is the number of μmoles of H2O2 produced per min) and the Km of the α-GPO for its substrate, L-α-glycerol-3-phosphate, was $1.5 \times 10 -2$mM.

'Partial purification of enzyme from Propionibacterium freudenreichii subso freudenreichii (DSM 20270)'

The supernatant from the high speed centrifugation (150,000 ×g for 90 minutes) containing purified α-GPO was applied to a chromatography column (1.6 ×88cm) containing Sephadex G-200 gel filtration resin. The proteins were eluted with 0.11M DMG buffer pH 5.5, the flow rate was 10ml $h-1$. The eluate was collected in 2ml fractions and was assayed by the previously described test system to determine the point of elution of the α-GPO activity. The α-GPO was found to elute in the void volume of the column with the molecular weight of 356,000. The specific activity of the pooled active fractions was 90 munits/mg protein and the Km of the α-GPO for its substrate L-α-glycerol-3-phosphate was $1.5 \times 10^{-2}$ mM.

'Determination of sub-unit molecular weight of enzyme from Propionibacterium freudenreichii subsp. freudenreichii (DSM 20270)'

Samples of the supernatant from the high speed centrifugation (150,000 ×g for 90 minutes) containing α-GPO were applied to a 10% non-denaturing polyacrylamide gel (PAGE). The samples were pre-treated with sucrose-saturated bromophenol blue to increase their density and contained approximately 50μg of protein. The gels were run at 4° C., 14 mamps for 16h. After running, the gels were dissected and stained for α-GPO activity and protein. The active bands were removed and denatured with 2% (w/v) sodium dodecyl sulphate and mercaptoethanol. A 7.5% PAGE gel was prepared containing 0.4% (w/v) SDS and the denatured α-GPO loaded. The gels were run at 200 volts for 5h and then stained for protein using Coomassie blue. Molecular weight standards were run at the same time to obtain a calibration curve. The sub-unit molcular weight of α-GPO was estimated to be 63,000, consistent with the presence of 4–6, probably 6, sub-units in the intact enzyme.

'α-GPO from Propionibacterium acidi-propionici (formerly arabinosum) and Propionibacterium freudenreichii subsp. shermanii (formerly P. shermanii)'

Freeze-dried cultures of 'P. acidi-propionici'(formerly 'arabinosum') NCIMB 5958) and 'P. freudenreichii' subsp. 'shermanii'(formerly 'P. shermanii') (NCIMB 9885) were obtained from the National Collection of Industrial and Marine Bacteria, Torry Research Station, Aberdeen, Scotland. The organisms were grown in a similar manner to that described above for 'P. freudenreichii' subsp. 'freudenriechii' (DSM 20270). The microorganisms were harvested, disrupted and assayed for α-GPO again in a similar way to 'P. 'freudenreichii' subsp. 'freudenreichii' (DSM 20270). The activities of the α-GPO in the cell-free extracts were 1.41 and 3.12 U (L culture)−1 and the Km values of the α-GPO for its substrates L-α0glycerol-3-phosphate were 1.8 and $2.2 \times 10^{-2}$ mM (18μM and 22μM) for 'P. acidi-propionici' (formerly 'arabinosum') (NCIMB 5958) and 'P. freudenreichii' subsp. 'shermanii' (formerly 'P. shermanii') (NCIMB 9885), respectively.

Similar results were obtained as follows:

| | |
|---|---|
| P. freudenreichii subsp. freudenreichii (NCIMB 5959) | 26 μM |
| P. freudenreichii subsp. shermanii (NCIMB 5964) | 6 μM |
| P. freudenreichii subsp. shermanii (NCIMB 9416) | 18 μM |

As regards stability, GPO from the high-speed supernatant retained 50% of its activity on storage for 10 days in solution (10 mg protein/ml in Tris buffer) at 4° C. and 35% after 24 days. Storage at room temperature resulted in a 90% loss of activity over the first four days, while 20 days storage at −20° C. retained >90% activity.

We claim:

1. A process for the preparation of an enzyme having α-glycerol-3-phosphate oxidase activity characterized in that the α-glycerol-3-phosphate oxidase has a Km of less than 2.5 mM, wherein the process comprises culturing a Propionibacterium, harvesting and disrupting the cells, separating a cell-free extract and at least partially purifying the desired enzyme.

2. A method of oxidizing α-glycerol-3-phosphate comprising contacting α-glycerol-3-phosphate with an enzyme having α-glycerol-3-phosphate oxidase activity, characterized in that the α-glycerol-3-phosphate oxidase has a Km of less 2.5 mM, and wherein said enzyme is obtained from a Propionibacterium, wherein said contacting occurs under conditions suitable for said oxidation to occur.

3. A process as claimed in claim 1, wherein the Km is less than 50 μM.

4. A method as claimed in claim 2, wherein the Km is less than 50 μM.

5. A process as claimed in claim 1, wherein the Propionibacterium is P, 'freudenreichii'subsp. 'freudenreichii, P. freudenreichii' subsp 'shermanii' or 'P. acidi-propionici.

6. A method as claimed in claim 2, wherein the Propionibacterium is 'P. freudenreichii'subsp. 'freudenreichii, P. freudenreichii'subsp. 'shermanii'or 'P. acidi-propionici.

7. A process as claimed in claim 1 wherein the Propionibacterium is 'P. freudenreichii'subsp. 'freudenreichii'(DSM 20270 or NCIMB 5959), or 'P. freudenreichii'subsp. 'shermanii'(NCIMB 9885, 5964 or 9416), or 'P. acidi-propionici'(NCIMB 5958) and has a Km of about 15μM, 26μM, 22μM, 6μM, 18μM or 18μM, respectively.

8. A method as claimed in claim 2 wherein the Propionibacterium is 'P. freudenreichii'subsp. 'freudenreichii'(DSM 20270 or NCIMB 5959), 'P. freudenreichii'subsp. 'shermanii'(NCIMB 9885, 5964 or 9416), or 'P. acidi-propionici'(NCIMB 5958) and has a Km of about 15,μM, 26μM, 22μM, 6μM, 18μM or 18μM, respectively.

* * * * *